United States Patent
Wang

(10) Patent No.: US 6,650,925 B2
(45) Date of Patent: Nov. 18, 2003

(54) METHOD FOR IMAGE GENERATION BY MAGNETIC RESONANCE

(75) Inventor: Jianmin Wang, Erlangen (DE)

(73) Assignee: Siemens Aktiengesellschaft, Münich (DE)

( * ) Notice: Subject to any disclaimer, the term of this patent is extended or adjusted under 35 U.S.C. 154(b) by 0 days.

(21) Appl. No.: 10/072,347

(22) Filed: Feb. 8, 2002

(65) Prior Publication Data

US 2002/0111549 A1 Aug. 15, 2002

(30) Foreign Application Priority Data

Feb. 14, 2001 (DE) .......................... 101 06 830

(51) Int. Cl.$^7$ .............................. A61B 5/055
(52) U.S. Cl. ................ 600/410; 324/307; 324/309
(58) Field of Search ................... 600/410, 407, 600/422; 324/307, 309, 318

(56) References Cited

U.S. PATENT DOCUMENTS

| 5,864,234 A | 1/1999 | Lüdeke |
| 5,910,728 A | 6/1999 | Sodickson |
| 6,255,821 B1 | 7/2001 | Oppelt |
| 6,289,232 B1 * | 9/2001 | Jakob et al. ............... 600/410 |
| 6,522,140 B2 * | 2/2003 | Harvey ...................... 324/307 |

FOREIGN PATENT DOCUMENTS

WO   WO 99/54746   10/1999

OTHER PUBLICATIONS

"An Algorithm For Rapid Image Acquisition Using Multiple Receiver Coils," Kelton et al, Proc. of the SMRM 8th Annual Meeting, Amsterdam (1989) p. 1172.
"Fast Imaging Method Using Multiple Receiver Coils With Subencoding Data Set," Ra et al Proc. SMRM 10th Annual Meeting, San Francisco (1991) p. 1240.
"Fast Imaging Using Subencoding Data Sets From Multiple Detectors," Ra et al, Magnetic Resonance in Medicine, vol. 30 (1993), pp. 142–145.
"AUTO–Smash: A Self–Calibrating Technique For SMASH Imaging," Jakob et al, Magn. Res. Mat. Phys, Biolog, Med., vol. 7 (1998) pp. 42–54.

* cited by examiner

Primary Examiner—Ruth S. Smith
(74) Attorney, Agent, or Firm—Schiff Hardin & Waite

(57) ABSTRACT

In a method for image generation by magnetic resonance, a number of independent reception antennas having sensitivity profiles differing from one another are employed, and radio-frequency excitation pulses and gradient pulses are emitted into an imaging volume for generating location-coded magnetic resonance signals. The magnetic resonance signals are received with the reception antennas, and respective k-space data sets each having middle rows and outer rows are formed from the reception signals of the respective reception antennas. The middle k-space rows are more densely arranged than the outer k-space rows in the respective k-space data sets. An intermediate image is reconstructed from each k-space data set. The sensitivity profiles from the middle k-space data rows are determined and the intermediate images are combined dependent on the sensitivity profiles to form an overall image.

7 Claims, 2 Drawing Sheets

METHOD FOR IMAGE GENERATION BY MAGNETIC RESONANCE

BACKGROUND OF THE INVENTION

1. Field of the Invention

The present invention is directed to a method for generating an image by magnetic resonance, and in particular to such a method employing a number of reception antennas, for picking up magnetic resonance signals, the respective antennas having different sensitivity profiles.

2. Description of the Prior Art

In the measurement sequences for magnetic resonance imaging that have been standard, and employed with a given size and resolution of the imaging, the time required for generating a magnetic resonance image is defined by the intensity of the gradient magnetic field used for the topical resolution. The gradient coils with which the gradient magnetic field is generated are becoming increasingly powerful and the measurements are becoming increasingly faster as a result. However, a physiologically prescribed limit human tissue (stimulation limit) that cannot be transgressed exists because of the magnetic fields that are rapidly switched in such sequences and because of the electrical voltages that are thereby induced in the tissue of the patient.

Recently, methods have been developed that are referred to as coil sensitivity and coding methods, or partial parallel acquisition (PPA). These methods use the sensitivity profiles of the individual antennas of an antenna array in order to reduce the phase-coding steps needed for the topical resolution and to thus shorten the measurement time.

Thus, the article by Hutchinson and Raff, "Fast MRI Data Acquisition Using Multiple Detectors", in Magnetic Resonance in Medicine, Vol. 6, pp. 87–91 (1988), describes a method wherein only one phase-coding step is required for producing an image. An antenna array having a number of independent individual antennas and radio-frequency channels is employed, the number corresponding exactly to the number of phase-coding steps given conventional, sequential phase-coding with phase-coding gradient fields. This method is difficult to employ because of the high number of required reception channels.

The article by James R. Kelton, Richard L. Magin, Steven M. Wright, "An Algorithm For Rapid Image Acquisition Using Multiple Receiver Coils", Proceedings of the SMRM 8th Annual Meeting, Amsterdam, 1989, p. 1172, describes a measuring method wherein the idea of Hutchinson and Raff was expanded. The number of individual antennas in the antenna array described therein amounts to a power of two. The measuring time is reduced corresponding to this number. The number of independent radio-frequency reception channels can be selected significantly lower then the number of phase-coding steps otherwise required for the image determination.

J. B. Ra and C. Y. Rim, in the article "Fast Imaging Method Using Multiple Receiver Coils with Sub-Encoding Data Set", which appeared in Proceedings of the SMRM 10th Annual Meeting, San Francisco, 1991, p. 1240, have described a method wherein, despite an under-sampling in the phase-coding direction, an unambiguous, convolution-free imaging of a region to be imaged (field of view) can be achieved. To this end, the reception signals of a number of independent reception antennas are reconstructed into intermediate images using a Fourier transformation, but these intermediate images are still ambiguous. Using the sensitivity profiles of the antennas employed, these intermediate images are processed to form a convolution-free ultimate image.

As reported in the article by J. B. Ra, C. Y. Rim, "Fast Imaging Using Sub-Encoding Data Sets from Multiple Detectors", in Magnetic Resonance in Medicine, Vol. 30, pp. 142–145, 1993, the method outlined above was tested at a phantom with a four-channel system. A speed-up of the measuring time with a factor of 4 was thereby achieved. A method also is described in this article with which the speed-up factor can be selected lower then the number of independent reception antennas.

A development of the fast imaging method described by Kelton et al and Ra/Rim is disclosed in PCT Application WO 99/54746. The inverse sensitivity matrices required in the processing of the intermediate images are replaced in this version by generalized inverse sensitivity matrices. For defining the sensitivity profiles required for the reconstruction of the ultimate image, a reference measurement having the same or a lower resolution as in the actual image production is implemented before the actual registration. To that end, the magnetic resonance signals are measured with the individual antennas in the antennas array as well as with the whole-body antenna permanently installed in the magnetic resonance apparatus. The sensitivity profile of the whole-body antenna is constant enough in order to be able to be used as a reference. The complex images (in the mathematical sense) of the individual antennas obtained after the Fourier transformation and the reference image of the whole body antenna are placed into relationship with one another, and the complex sensitivity profiles (in the mathematical sense) of the individual antennas are obtained. These are then employed for the reconstruction in the following, actual measurement. A disadvantage of this version is that the required measuring time is lengthened by the "pre-scan". It generally applies in the measurement of magnetic resonance images that the signal-to-noise ratio is proportional to the square root of the measurement time. Since the pre-scan, however, is employed only in order to determine the sensitivity profiles of the individual antennas in the antenna array, the signal-to-noise ratio is not improved despite a lengthened measurement time. The relationship of the signal-to-noise ratio to the square root of the measurement time is poorer in this version than in conventional methods when the measurement time required for the pre-scan is also taken into consideration.

U.S. Pat. No. 5,910,728 discloses another method with which the measurement time can be reduced by omitting phase-coding steps. An antenna array having independent individual antennas is also employed therein. The reconstruction of the missing phase-coding steps ensues, however, in the spatial frequency domain (k-space) and not in the image space as in the above methods. Due to the specific type of reconstruction of the missing k-space rows, this method is also called SMASH (simultaneous acquisition of special harmonics). It is assumed, however, that the sensitivity profiles of the individual antennas do not vary greatly in the frequency coding direction. Another pre-requisite for a convolution-free reconstruction of a magnetic resonance image is an exact knowledge of the sensitivity profiles of the individual antennas employed. Since the sensitivity profiles are also patient-dependent, they must usually be measured with each patient in the examination position.

In the method described in the article by P. M. Jakob, M. A. Griswold, R. R. Edelman, D. K. Sodickson, "AUTO SMASH: A self-calibrating technique for SMASH imaging", in 1998 in Magnetic Resonance Materials in Physics, Biology and Medicine, Vol. 7, pages 42–54, a calibration step with a corresponding phase-coding is implemented in addition to the reduced SMASH phase-coding steps. The sensitivity profiles of the individual antennas are determined therefrom during the measurement, and the correlation between the under-sampled SMASH signals and the additional calibration signals is analyzed.

SUMMARY OF THE INVENTION

An object of the present invention is to provide a method for fast image generation by means of magnetic resonance, whereby the sensitivity profiles of the individual antennas in the antenna array are determined in a simple way.

This object is achieved in accordance with the invention in a method for image generation by magnetic resonance, wherein a number of independent reception antennas having sensitivity profiles differing from one another are employed, and wherein in radio-frequency excitation pulses and gradient pulses are emitted into an imaging volume for generating location-coded magnetic resonance signals, the magnetic resonance signals are received with the reception antennas, with a k-space data set having middle and outer k-space rows being formed from the reception signals of each reception antenna, the middle k-space rows being more densely arranged than the outer k-space rows in the k-space data set, an intermediate image is reconstructed from each k-space data set, the sensitivity profiles are determined from the middle k-space data rows, and the intermediate images are combined dependent on the sensitivity profiles to form an overall image.

In this method, the measurement steps for determining the sensitivity profiles of the individual antennas are integrated into the actual measurement. This ensues by the k-space in the low spatial frequency range being completely occupied in phase-coding direction using the phase-coding gradient fields. Outside this region, i.e. in the region of high spatial frequencies, the phase-coding steps are reduced according to the methods proposed by Ra/Rim or Kelton et al in order to reduce the measurement time.

Individual images having a rough (coarse) resolution are then reconstructed from the magnetic resonance signals in the low spatial frequency range, these individual images being allocated to the corresponding individual antennas. Since the sensitivity profiles of the individual antennas are themselves mainly composed of low spatial frequency components, the information needed for determining the sensitivity profiles is thus completely identified. No additional information beyond the sensitivity profiles of the individual antennas is required.

The entire measurement time is lengthened somewhat as a result. The additional phase-coded magnetic resonance signals in the middle region of the k-space, however, can be employed for enhancing the signal-to-noise ratio, and thus for improving the imaging quality for the reconstruction of the individual images as well, and thus of the overall image. It is also a particular advantage that the sensitivity profiles are derived from the same measurement as the signals acquired for the actual image generation; this method therefore functions for determining the sensitivity profiles even given sequences with more pronounced topical distortion. One example of this is the EPI sequence (EPI is an abbreviation for echo planar imaging). It is known that image artifacts referred to as blurring artifacts or distortions occur given fast EPI sequences. Since the reference images exhibit the same distortions, the reconstruction also functions given more pronounced topical distortion.

It should be noted out that filters are required in the case of a method with a pre-scan in order to obtain noise-free coil profiles. These filters must be adapted to the size of the field of view and to the coil size, which requires a certain outlay for the implementation. In contrast, the coil profiles need not be filtered in the inventive method. The employment of signals from only the middle region of the k-space corresponds to a low-pass filtering.

DESCRIPTION OF THE PREFERRED EMBODIMENTS

Figure 1:
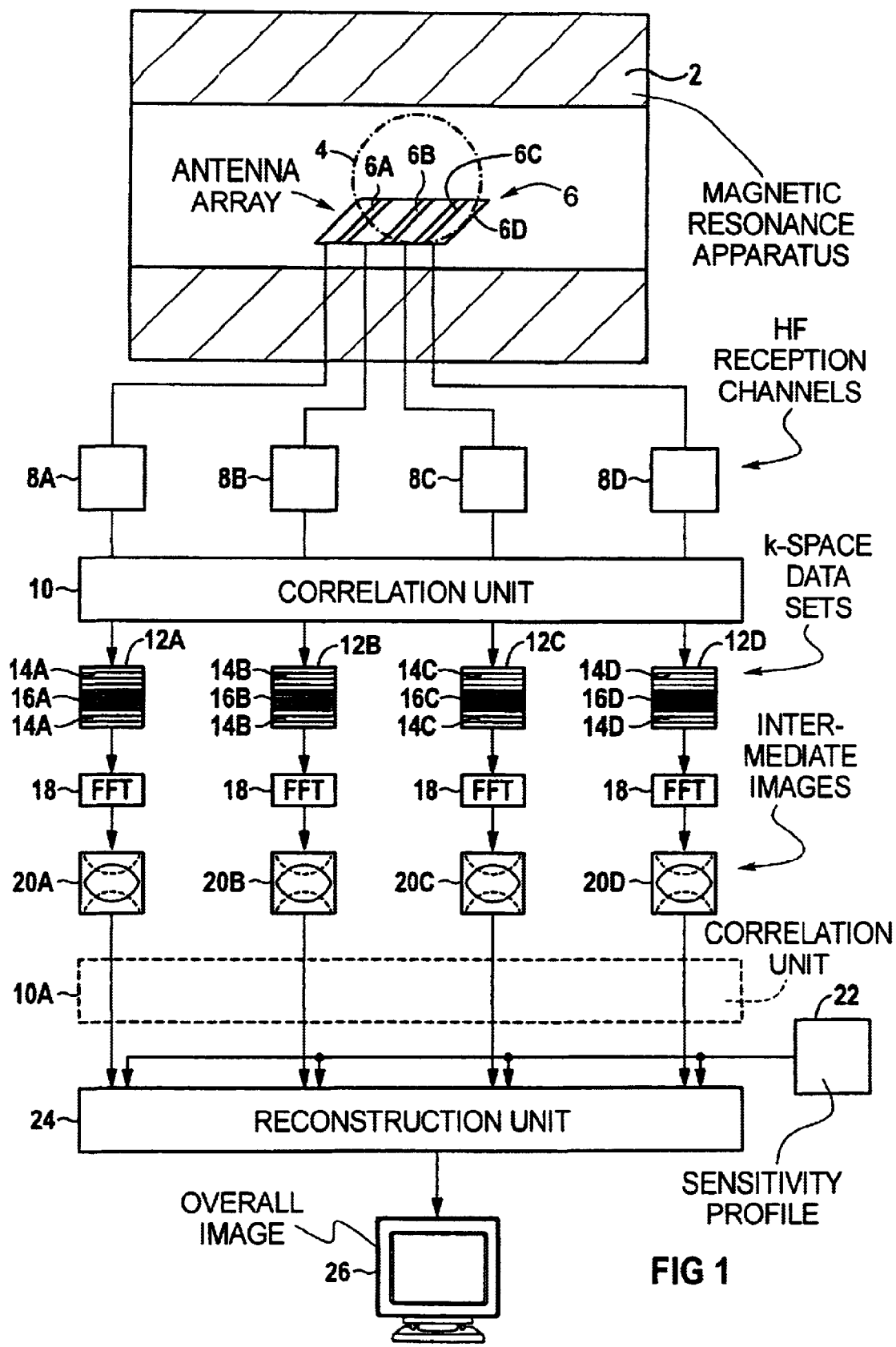
FIG. 1 is an overall illustration showing the basic steps in the signal processing for fast magnetic resonance imaging in accordance with the inventive method.

FIG. 1 schematically shows a diagnostic magnetic resonance apparatus 2 having the known (and therefore not individually illustrated) components of a basic field magnet for generating a uniform magnetic field in an imaging volume 4, a gradient system for generating magnetic gradient fields in three spatial directions residing perpendicularly to one another, a radio-frequency antenna system for exciting and for receiving magnetic resonance signals, as well as a control unit for controlling the individual components in the magnetic resonance apparatus. Dependent on a selected sequence, the magnetic gradient fields are activated for location coding of the magnetic resonance signals at predetermined time intervals with a predetermined intensity. A distinction is made between a slice selection gradient, a phase code gradient and a frequency coding gradient. In many sequences, thus, only the nuclei in one layer are excited by the slice coding gradient field being simultaneously activated with a radio-frequency excitation pulse. A further location coding then ensues in the excited slice in phase-coding direction by activating the phase-coding gradient. The phase of the magnetic resonance signal is determined by the gradient time area of the phase-coding gradient. Finally, a frequency coding in a direction perpendicular to the phase-coding ensues upon reception of the magnetic resonance signal by activating the frequency coding gradient. The radio-frequency antenna system has a whole-body antenna that is fashioned for the excitation as well as for the reception of the magnetic resonance signals. Additionally, an antenna array 6 having individual antenna 6A, 6B, 6C, 6D independent of one another is present, these, in contrast to the whole-body antenna, each being capable of imaging only a limited area. This is exploited in a fast magnetic resonance imaging method with parallel data acquisition, whereby the location coding in phase-coding direction no longer need completely ensue with phase-coding gradients. These methods are known as described, for example, in the initially cited article by Kelton et al. The individual antennas 6A, 6B, 6C, 6D are respectively connected to independent radio-frequency channels 8A, 8B, 8C, 8D wherein an amplification, a phase-sensitive demodulation and a digitizing of the magnetic resonance signal respective received from the individual antennas 6A, 6B, 6C, 6D ensues.

The reception channels 8A, 8B, 8C, 8D are connected to a correlation unit 10 with which the further-processed signals from the reception channels are de-correlated with respect to noise. An optimum signal-to-noise ratio thus is achieved in the following reconstruction, which shall be described in yet greater detail below. To that end, a noise correlation matrix COR is used that previously determined from the pure noise reception signals of the individual antennas 6A, 6B, 6C, 6D. A de-correlation matrix K is determined from the inverted matrix $COR^{-1}$ of the noise correlation matrix COR, the de-correlation matrix K containing weighting factors in order to de-correlate the actual information carrying signals from one another with respect to the noise. For determining this de-correlation matrix, noise reception signals $X_1(t)$, $X_2(t)$, $X_3(t)$, $X_4(t)$ of the individual antennas 6A, 6B, 6C, 6D are further-processed according to the following, general relationships following a phase-sensitive demodulation.

The noise reception signals $X_1(t)$, $X_2(t)$, $X_3(t)$, $X_4(t)$ can be presented as column vector X(t). The elements of the noise correlation matrix COR can be determined as a matrix product of the column vector X(t) with a row vector $X^*(t)$, whose components form the complex conjugated noise reception signals X(t), as well as a subsequent integration over the time. The de-correlation matrix K having the weighting factors for the noise de-correlation of the actual measured signals is derived from the square root of the inverted noise correlation matrix $COR^{-1}$.

The reception signals are then read into the appertaining rows of respective k-space matrices 12A, 12B, 12C, 12D according to their phase-coding prescribed by the phase-coding gradient, and thus form respective k-space data sets. The number of phase-coding steps is thus reduced for the regions of higher spatial frequencies, i.e. in outer regions 14A, 14B, 14C, 14D, compared to conventional sequences. The rows in these regions of the k-space matrices 12A, 12B, 12C, 12D thus are not completely occupied (filled) with signals. In contrast, k-space is completely occupied in the regions of lower spatial frequencies, i.e. in the middle k-space regions 16A, 16B, 16C, 16D of k-space. Via a fast Fourier transformation 18, respective intermediate images 20A, 20B, 20C, 20D are generated from the signals in only partially completely occupied k-spaces. These intermediate images 20A, 20B, 20C, 20D include convolutions because of the under-sampling in phase-coding direction. For example, a circular structure in the image would still be superimposed by two shifted semicircles, as highly schematically shown in FIG. 1.

Instead of being applied in the spatial frequency domain, as set forth above, the noise de-correlation can be applied with the same result to the intermediate images 20A, 20B, 20C, 20D in the image space with the same result. The correlation unit in FIG. 1 is then eliminated; instead, a correspondingly adapted correlation unit 10A is employed, this being shown with broken lines in FIG. 1.

Using the complex coil profiles 22 (in the mathematical sense) of the individual antennas 6A, 6B, 6C, 6D, a convolution-free overall image 26 of the examination region is generated from the intermediate images 20A, 20B, 20C, 20D in a reconstruction unit 24. The reconstruction method has been described elsewhere, for example in Kelton et al, and essentially involves determining the values for the picture elements of the overall image 26 from the corresponding picture elements of all intermediate images 20A, 20B, 20C, 20D on the basis of a weighted summing. The weighting factors represent a matrix is derived by inversion from the complex sensitivity matrices of the individual antennas 6A, 6B, 6C, 6D.

Figure 2:
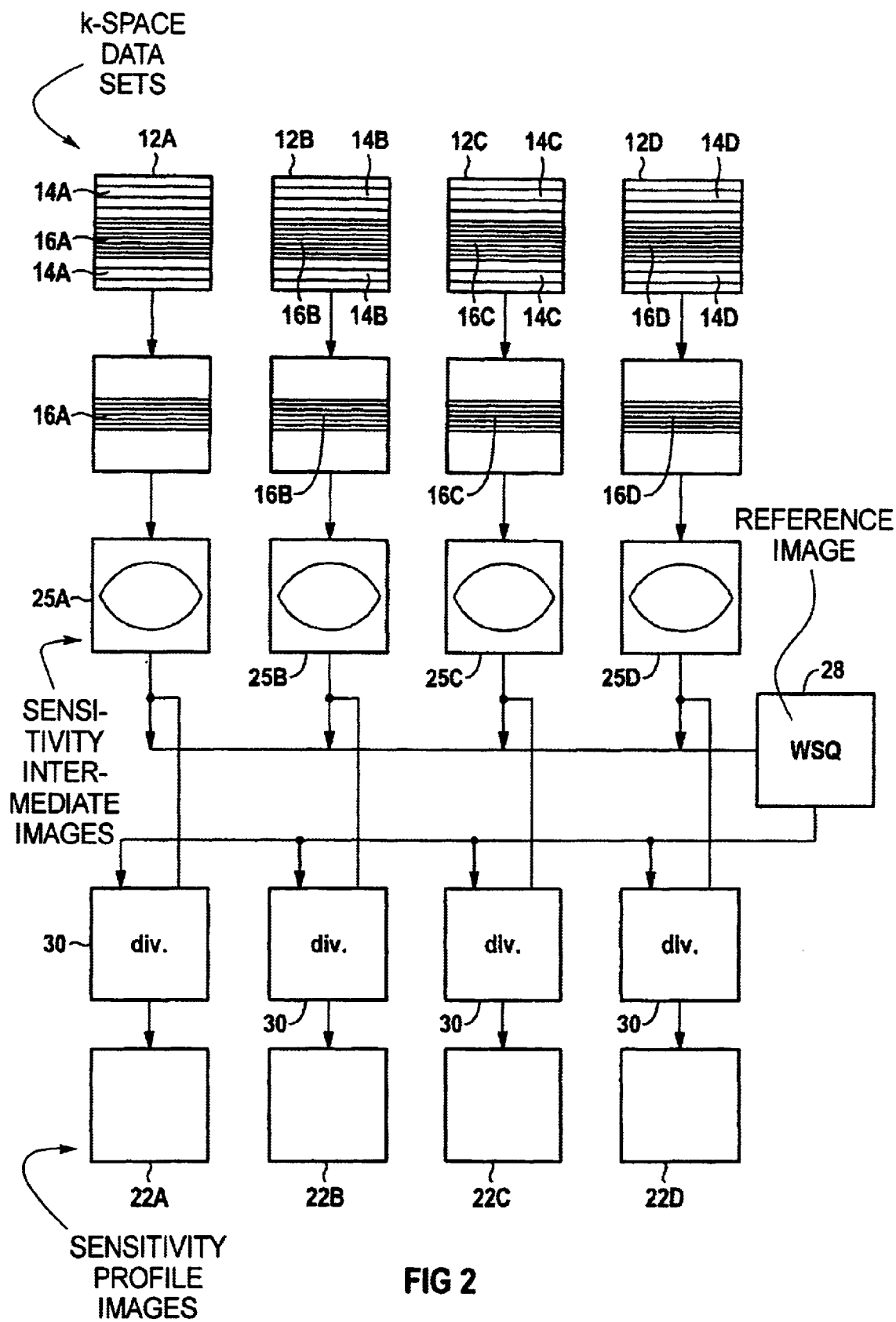
FIG. 2 is an overall illustration showing the essential signal processing step for determining the coil profiles from the signals employed for the imaging in accordance with the inventive method.

The method for determining the complex sensitivity profiles of the individual antennas 6A, 6B, 6C, 6D is now explained with reference to FIG. 2. As set forth above, the phase-coding steps are selected in the generation of the magnetic resonance signals such that the middle region of each k-space 16A, 16B, 16C is completely occupied with values. Sensitivity intermediate images 25A, 25B, 25C, 25D having a coarse resolution are now reconstructed from the middle k-space rows. A sum image 28 that is used as a reference image is also formed from the individual sensitivity intermediate images 25A, 25B, 25C, 25D.

The sensitivity intermediate images 25A, 25B, 25C, 25D respectively contain picture elements that are characterized by numerical values. For example, the square root of the sum of the squares of the individual sensitivity intermediate images 25A, 25B, 25C, 25D can be employed as the sum image 28. A quotient formation 30 of the individual images 25A, 25B, 25C, 25D divided by the reference image 28 respectively yields the sensitivity profiles 20A, 20B, 20C, 20D of the individual antenna elements 6A, 6B, 6C, 6D. As a result of the quotient formation 30, the tissue contrast generated by the anatomy disappears. The pure sensitivity profiles 20A, 20B, 20C, 20D remain, these then being employed for reconstruction of the image 26 with the reduced phase-coding steps.

Particularly suited as measurement sequence are all sequences that already inherently have a short measurement duration in order, proceeding from these sequences, to reduce the measurement time further, for example, EPI or FISP sequences are well suited for this reason.

Given an FISP sequence (fast imaging with steady precession), for example, a high signal is also achieved given short pulse repetition times as a result of a complete rephasing of the spins. A refocusing gradient pulse is thereby applied in phase-coding direction.

For illustrating the gain in measurement time to be achieved compared to a traditional signal acquisition, let a rectangular magnetic resonance image be generated as example having a resolution of 256 picture elements in the frequency coding direction and a resolution of 192 picture elements in the phase-coding direction. The individual phase-coding steps are selected, for example, such that k-space is completely occupied with 48 k-space rows in the low spatial frequency range. This corresponds to one-fourth of the k-space rows that would be required for a conventional convolution-free reconstruction. Outside of this middle region, the k-space is occupied with a plurality of rows reduced by the factor 2, this corresponding to a correspondingly reduced number of phase-coding steps. (196−48)/2=72 rows are thus generated.) The image reconstructed from the individual intermediate images (for example, four intermediate images) is convolution-free. The reduction in measurement time in this case amounts to 192/(72+48)=1.6. Compared to an image that is reconstructed from a completely occupied k-space, the signal-to-noise ratio (S/N) is only degraded by the factor $\sqrt{1.6}$.

Although modifications and changes may be suggested by those skilled in the art, it is the intention of the inventor to embody within the patent warranted hereon all changes and modifications as reasonably and properly come within the scope of the inventor's contribution to the art.

I claim as my invention:

1. A method for generating an image by magnetic resonance, comprising the steps of:

emitting radio-frequency excitation pulses into an imaging volume for exciting nuclear magnetic resonance signals in said imaging volume;

generating at least one gradient field in said imaging volume for location-coding said nuclear magnetic resonance signals to produce location-coded magnetic resonance signals;

receiving said location-coded magnetic resonance signals with a plurality of independent reception antennas, each having a sensitivity profile, with the respective sensitivity profiles of said reception antennas differing from each other, said reception antennas respectively generating reception signals;

generating a plurality of k-space data sets respectively from the reception signals from the plurality of reception antennas, each k-space data set having middle k-space rows and outer k-space rows, with said middle k-space rows being more densely disposed in said k-space data set than said outer k-space rows;

reconstructing a plurality of intermediate images respectively from said k-space data sets;

for each k-space data set, constructing a sensitivity intermediate image from the middle k-space rows of that k-space data set, to obtain a plurality of sensitivity intermediate images;

combining said plurality of sensitivity intermediate images to form a reference image;

for each of said reception antennas, determining a sensitivity profile by identifying a relationship to said reference image of the sensitivity intermediate image in said plurality of sensitivity intermediate images constructed from the k-space data set generated from the reception signal for that antenna; and combining said intermediate images dependent on said sensitivity profiles to form an overall image of at least a portion of said imaging volume.

2. A method as claimed in claim 1 wherein each of said sensitivity intermediate images and said reference image is comprised of picture elements, with each picture element in each image having a numerical value associated therewith, and wherein said reference image is formed by generating picture elements having respective numerical values which are a sum of the squares of the numerical values of the corresponding picture elements in the respective sensitivity intermediate images.

3. A method as claimed in claim 2 wherein the picture elements in reference image have respective numerical values which are a square root of said sum.

4. A method as claimed in claim 1 comprising the additional step of de-correlating said k-space data sets relative to each other with regard to noise signals.

5. A method as claimed in claim 1 comprising the additional step of de-correlating said intermediate images relative to each other with regard to noise signals.

6. A method for generating an image by magnetic resonance, comprising the steps of:

emitting radio-frequency excitation pulses into an imaging volume for exciting nuclear magnetic resonance signals in said imaging volume;

generating at least one gradient field in said imaging volume for location-coding said nuclear magnetic resonance signals to produce location-coded magnetic resonance signals;

receiving said location-coded magnetic resonance signals with a plurality of independent reception antennas, each having a sensitivity profile, with the respective sensitivity profiles of said reception antennas differing from each other, said reception antennas respectively generating reception signals;

generating a plurality of k-space data sets respectively from the reception signals from the plurality of reception antennas, each k-space data set having middle k-space rows and outer k-space rows, with said middle k-space rows being more densely disposed in said k-space data set than said outer k-space rows, and decorrelating said k-space data sets relative to each other with regard to noise signals;

reconstructing a plurality of intermediate images respectively from said k-space data sets;

identifying the respective sensitivity profile for each of said reception antennas from the middle k-space rows of the k-space data set respectively generated from the reception signal from that reception antenna; and combining said intermediate images dependent on said sensitivity profiles to form an overall image of at least a portion of said imaging volume.

7. A method for generating an image by magnetic resonance, comprising the steps of:

emitting radio-frequency excitation pulses into an imaging volume for exciting nuclear magnetic resonance signals in said imaging volume;

generating at least one gradient field in said imaging volume for location-coding said nuclear magnetic resonance signals to produce location-coded magnetic resonance signals;

receiving said location-coded magnetic resonance signals with a plurality of independent reception antennas, each having a sensitivity profile, with the respective sensitivity profiles of said reception antennas differing from each other, said reception antennas respectively generating reception signals;

generating a plurality of k-space data sets respectively from the reception signals from the plurality of reception antennas, each k-space data set having middle k-space rows and outer k-space rows, with said middle k-space rows being more densely disposed in said k-space data set than said outer k-space rows;

reconstructing a plurality of intermediate images respectively from said k-space data sets, and decorrelating said intermediate images relative to each other with regard to noise signals;

identifying the respective sensitivity profile for each of said reception antennas from the middle k-space rows of the k-space data set respectively generated from the reception signal from that reception antenna; and combining said intermediate images dependent on said sensitivity profiles to form an overall image of at least a portion of said imaging volume.

* * * * *